US009522228B2

(12) United States Patent
Teutsch et al.

(10) Patent No.: US 9,522,228 B2
(45) Date of Patent: Dec. 20, 2016

(54) DEVICE FOR INSERTING AN INSERTION MEMBER, OR A SOFT MEMBER, INTO BODY TISSUE

(71) Applicant: Roche Diagnostics International AG, Rotkreuz (CH)

(72) Inventors: David Teutsch, Schuepfen (CH); Christoph Huwiler, Arth (CH); Philipp Michel, Kirchlindach (CH); Heiner Kaufmann, Bern (CH)

(73) Assignee: Roche Diagnostics International AG (CH)

( * ) Notice: Subject to any disclaimer, the term of this patent is extended or adjusted under 35 U.S.C. 154(b) by 791 days.

(21) Appl. No.: 13/714,227

(22) Filed: Dec. 13, 2012

(65) Prior Publication Data

US 2013/0102965 A1 Apr. 25, 2013

Related U.S. Application Data

(63) Continuation of application No. PCT/CH2011/000124, filed on May 26, 2011.

(30) Foreign Application Priority Data

Jun. 21, 2010 (EP) .................................... 10006420
Jun. 21, 2010 (EP) .................................... 10006421

(51) Int. Cl.
*A61M 5/158* (2006.01)

(52) U.S. Cl.
CPC .................................... *A61M 5/158* (2013.01)

(58) Field of Classification Search
CPC ..................... A61M 5/158; A61M 2005/1581; A61M 2005/1585; A61M 2005/1586; A61M 2005/1587; A61M 25/02; A61M 25/0631; A61M 25/0606; A61B 17/3415

(Continued)

(56) References Cited

U.S. PATENT DOCUMENTS 7,850,652 B2   12/2010   Liniger et al.
7,896,844 B2    3/2011   Thalmann et al.
(Continued)

FOREIGN PATENT DOCUMENTS

CH   WO 2008022476 A1 *   2/2008  ............ A61M 5/158
EP        1764125 A1         3/2007
(Continued)

OTHER PUBLICATIONS

European Search Report, EP 15 19 7830, dated Feb. 19, 2016.

*Primary Examiner* — Kevin C Sirmons
*Assistant Examiner* — Amber Stiles
(74) *Attorney, Agent, or Firm* — Bose McKinney & Evans LLP

(57) ABSTRACT

A soft cannula is inserted into tissue and affixed to skin. A cannula arrangement moves within a housing and provides the soft cannula and a guiding needle extending through the cannula to temporarily stiffen it. A drive effects an insertion movement of the cannula arrangement from a first position, where a puncturing tip is pulled back relative to a face of the housing, into a second position, where the puncturing tip protrudes beyond the face, and automatically effects a retracting movement of the guiding needle into a third position, where the puncturing tip is pulled back relative to the face. The face is formed by a base plate affixed to the housing so that when the cannula arrangement is in the second position, the face detaches from the housing. A holder element is connected to the soft cannula and couples to the base plate in the cannula arrangement's second position.

24 Claims, 7 Drawing Sheets

(58) Field of Classification Search
USPC ............ 604/164.01, 164.04, 164.08, 164.12, 174,604/192, 198, 508, 157
See application file for complete search history.

(56) References Cited

U.S. PATENT DOCUMENTS

| | | |
|---|---|---|
| 2002/0022855 A1 | 2/2002 | Bobroff et al. |
| 2004/0158207 A1 | 8/2004 | Hunn et al. |
| 2008/0228144 A1* | 9/2008 | Liniger ................. A61M 5/158 604/164.08 |
| 2008/0269687 A1 | 10/2008 | Chong et al. |
| 2008/0319414 A1* | 12/2008 | Yodfat et al. ................. 604/506 |
| 2009/0143763 A1 | 6/2009 | Wyss et al. |

FOREIGN PATENT DOCUMENTS

| | | |
|---|---|---|
| EP | 1970091 A1 | 9/2008 |
| EP | 20075217 A1 | 9/2008 |
| WO | 2007/140631 A1 | 12/2007 |

\* cited by examiner

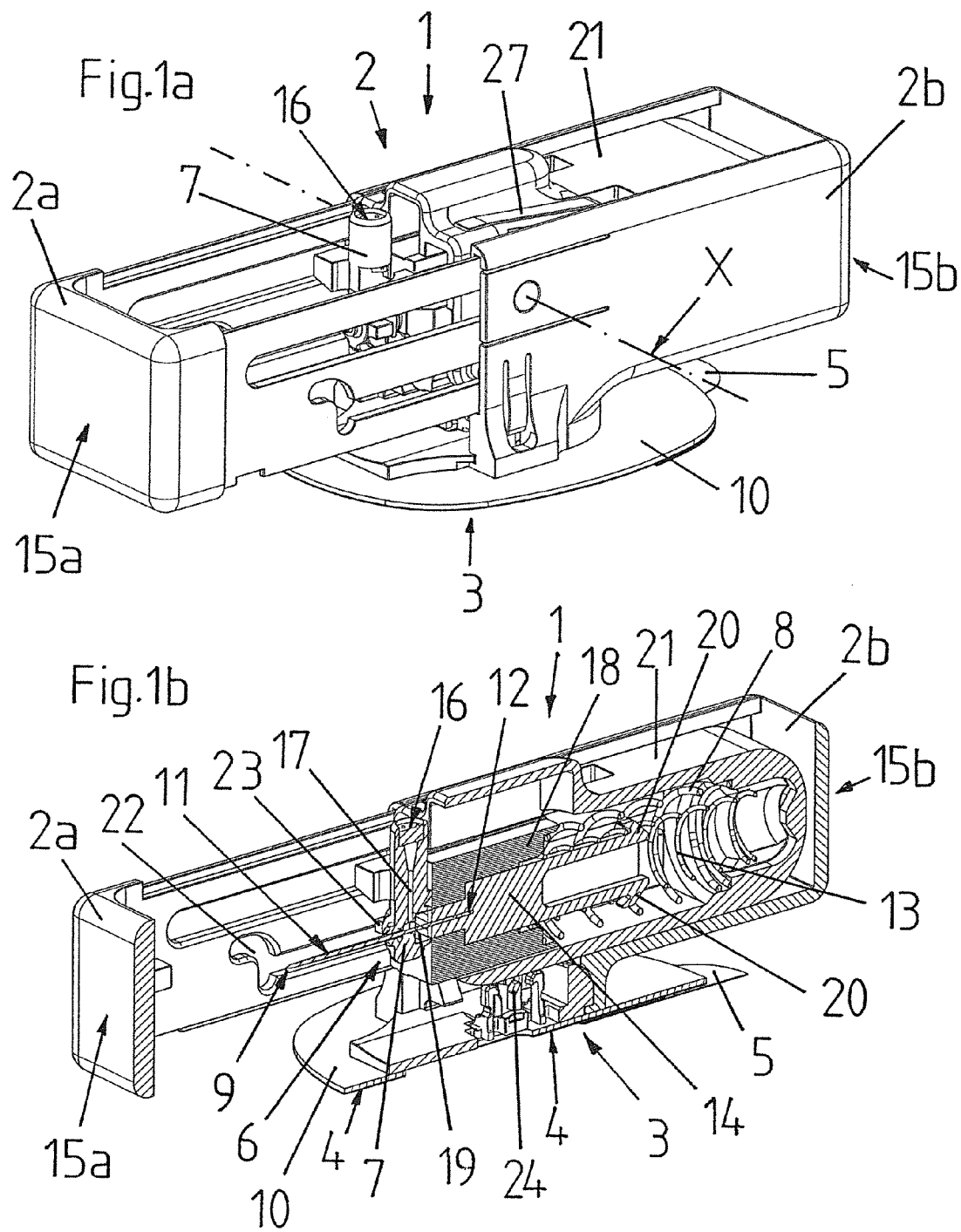

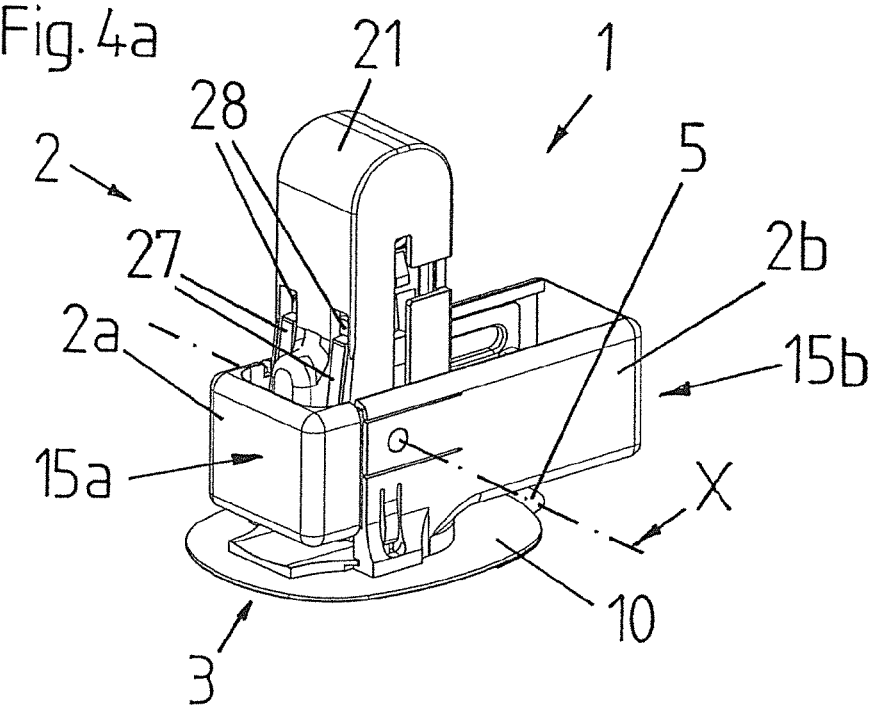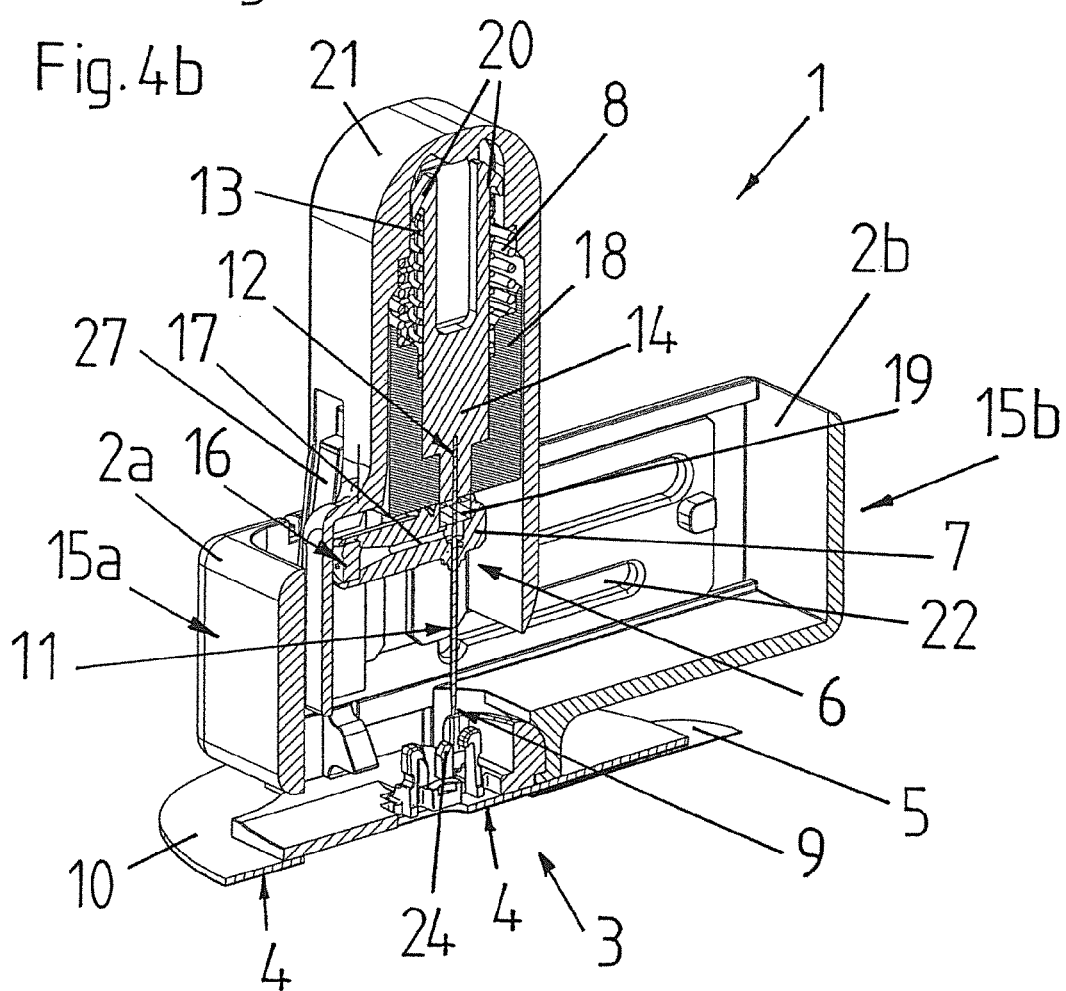

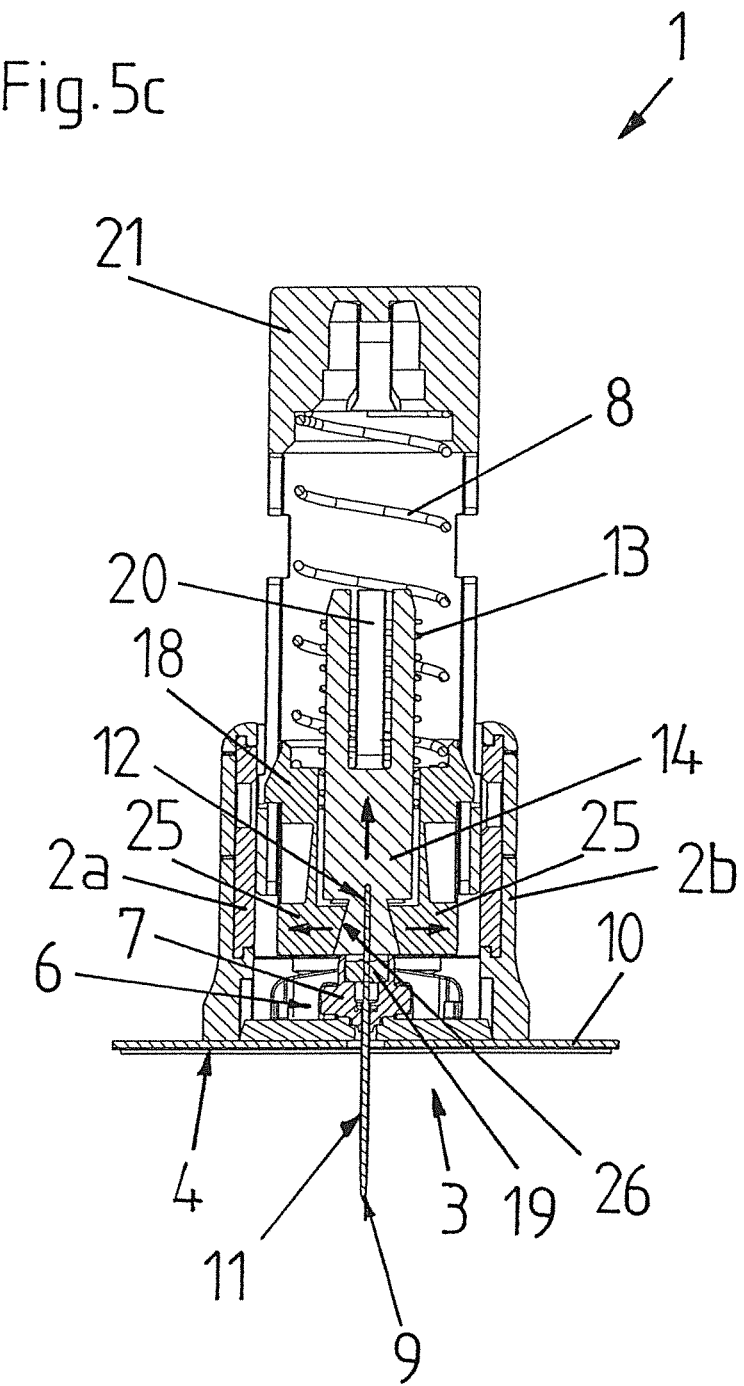

DEVICE FOR INSERTING AN INSERTION MEMBER, OR A SOFT MEMBER, INTO BODY TISSUE

CROSS-REFERENCE TO RELATED APPLICATIONS

This application is a continuation of PCT/CH2011/000124, filed May 26, 2011, which is based on and claims priority to EP 10006421.1, filed Jun. 21, 2010 and EP 10006420.3, filed Jun. 21, 2010, which are hereby incorporated by reference.

BACKGROUND

The present disclosure relates to a device and method for inserting at least one insertion member having a puncturing tip into body tissue a patient and for fixing it to the skin of the body. The present disclosure also relates to a device and method for inserting a soft member into the body tissue.

For patients with a regular requirement for a medication administered by direct delivery into the body tissue or into the blood stream, for example, patients suffering from pain or patients with type I or type II diabetes, it can be useful to supply the body with the required quantity of medication in liquid form via a cannula that is introduced at a suitable location into the body and that remains there over a period of time. For this purpose, a cannula arrangement, designated as an infusion set or port, depending on its design, is secured on the patient's skin in such a way that the cannula passes through the skin and into the body.

Efforts are also increasingly being made to monitor certain medical parameters of a patient, for example, the blood sugar value, continuously over a long period of time. For this purpose, a sensor arrangement, for example, is placed on the patient's body and, with a puncturing tip, a suitable sensor passes through the skin and into the patient's body.

To avoid infections, the infusion set, the port or the sensor arrangement should be changed at regular intervals, for example, every three days. In outpatient treatment, for example in the case of diabetics, this is often done by the patients themselves and, on account of the introduction of the infusion cannula or the puncturing tip, respectively, into the skin, is associated with a certain amount of pain. It is therefore important that such infusion sets, ports or sensor arrangements can be applied easily and safely, which may be why many manufacturers have started designing their products as insertion heads for special insertion devices with the aid of which these insertion heads can be applied to the patient's body.

Also, in order to keep irritation of the application site during the application period at a minimum, it is desirable that the cannula or sensor which is inserted into the body be soft, i.e. is designed as an element which can have certain flexibility so that it can follow certain movements of the body tissue. However, due to this structural flexibility, such cannulas and sensors require for their introduction into the body a guiding element which provides a puncturing tip and stiffens them during the introduction movement. Furthermore, after the introduction of the cannula or sensor into the body, the guiding element must be removed and disposed off in a safe manner since it is contaminated and contact with other persons could result in the transfer of diseases such as, in case of an accidental piercing of the skin of the person with the contaminated puncturing tip of the guiding element.

Some known insertion devices for applying infusion sets have a base plate attached by skin compatible glue to a patient's body. With these insertion devices, the infusion sets can be placed onto the application site of the body by the force of a pre-tensioned spring, so that the cannula of the infusion set abruptly penetrates into the body tissue and the infusion set with its base plate is affixed to the skin. Even though with these known insertion devices, the application of infusion sets can be made easier and due to the quick and targeted puncturing procedure, the pain associated with the application can be significantly reduced compared with a manual application, there is still a potential for further improvement. A further disadvantage of these devices is that the fixation of the infusion set to the skin often is unsatisfactory so that, after the application, the infusion set must be pressed by hand against the skin in order to ensure a proper affixation. This, however, can be associated with the risk that the cannula might be flexed or be partially pulled out of the tissue resulting in irritation of the application site.

Other known insertion devices for infusion sets with soft cannulas are stiffened by a guiding needle, by which the infusion set can be placed onto the application site by the force of a pre-tensioned spring so that the guiding needle with the cannula abruptly penetrates into the tissue. After application of the infusion set, the insertion device and the guiding needle are removed from the infusion set, either together or separately. In the case where the insertion head is applied by hand, after the application, the guiding needle is removed by gripping a holder connected to it and by pulling this holder in the opposite direction of the inserting direction of the cannula, thereby removing the guiding needle from the soft cannula. After the guiding needle is pulled out of the cannula, it is pivoted in a protected position within a housing forming the holder. In the case where the insertion head is applied with an insertion device, after the application either in a first step the insertion device is removed from the application site and after that in a second step the guiding needle is removed in the way described before or, in case a specific insertion device is used for applying the insertion head, in a first step the insertion device is removed together with the guiding needle and in a second step the guiding needle is released from the insertion device and after that is pivoted into a protected position within the housing forming the holder. While with the disclosed insertion devices the introduction of the soft cannula of the infusion set into the tissue of the body is considerable easy and safe, the removal of the guiding needle needs a certain sleight of hand and may cause irritation at the puncture site by forces exerted onto the inserted cannula if not performed properly. Furthermore, the removal of the guiding needle is associated with a certain risk of injury, since after its removal from the infusion set it is uncovered and must be handled with care. An application by hand in any case has the disadvantage that it needs certain skills and, since it is accompanied by a certain pain, costs the patient quite an effort.

Therefore, there is a need for a device where the application of an infusion set with a soft cannula becomes easy and safe even for unskilled persons. The insertion can take place at a higher speed compared to known devices, resulting in a reduction of the pain and a reduction in the risk of an irritation of the puncture site. In addition, the risk of an unintended contact with the contaminated guiding needle is substantially eliminated.

SUMMARY

According to the present disclosure, a device and method for inserting at least one insertion member having a puncturing tip into tissue of a patient and for affixing the at least one insertion member to the patient's skin. The device comprises a housing having at least one contact face for affixing the device onto the patient's skin, an insertion arrangement movably arranged within the housing comprising the at least one insertion member to be inserted into the tissue and a holder element fixedly connected with at least a part of the at least one insertion member which is intended to remain for a longer period inside the tissue of the body; and a drive arranged within the housing for effecting an insertion movement of the insertion arrangement from a first position, in which the puncturing tip of the at least one insertion member is pulled back relative to the contact face, into a second position, in which the puncturing tip of the at least one insertion member protrudes beyond the contact face, so that the at least one insertion member is inserted into the tissue of the patient when the device during the insertion movement of the insertion arrangement is placed with its contact face on the patient. The contact face is formed by a base plate affixed so that, after the insertion movement has been performed, the base plate detaches from the housing and wherein the holder element of the insertion arrangement is coupled to the base plate when the insertion arrangement by the insertion movement is brought into the second position.

In accordance with another embodiment of the present disclosure, a device for inserting soft member into the body tissue of a patient. The device comprises a housing having at least one contact face for placing the device onto the skin of the patient; an insertion arrangement movably arranged within the housing comprising the soft member to be inserted into the tissue and a guiding member for temporarily stiffening the soft member during introduction into the tissue, wherein the guiding member forms a puncturing tip for puncturing the skin when inserting the stiffened soft member with it into the tissue; and a drive for effecting an insertion movement of the insertion arrangement from a first position, in which the puncturing tip is pulled back relative to the contact face, into a second position, in which the puncturing tip protrudes beyond the contact face, so that, when during the insertion movement the device is placed with its contact face on the body, the soft member together with the guiding member is inserted into the tissue of the body of the patient and for effecting, after the insertion movement of the insertion arrangement, a retracting movement of the guiding member from the second position into a third position, in which its puncturing tip is pulled back relative to the contact face, so that, when the soft member is held in the second position, the guiding member is separated from the soft member. After the insertion movement of the insertion arrangement has been performed, the retraction movement of the guiding member is automatically performed.

Accordingly, it is a feature of the embodiments of the present disclosure to provide a device where the application of an infusion set with a soft cannula becomes easy and safe even for unskilled persons. The insertion can take place at a higher speed compared to known devices, resulting in a reduction of the pain and a reduction in the risk of an irritation of the puncture site. In addition, the risk of an unintended contact with the contaminated guiding needle is substantially eliminated. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which:

FIG. 1a illustrates a perspective view of a device according to an embodiment of the present disclosure.

FIG. 1b illustrates a perspective longitudinal section of the device of FIG. 1a according to an embodiment of the present disclosure.

FIG. 4a illustrates a perspective view of the device of FIG. 1a in a fourth state according to an embodiment of the present disclosure.

FIG. 4b illustrates a perspective longitudinal section of the device of FIG. 4a according to an embodiment of the present disclosure.

FIG. 5c illustrates a cross section of the device of FIG. 5a according to an embodiment of the present disclosure.

DETAILED DESCRIPTION

Figure 2A:
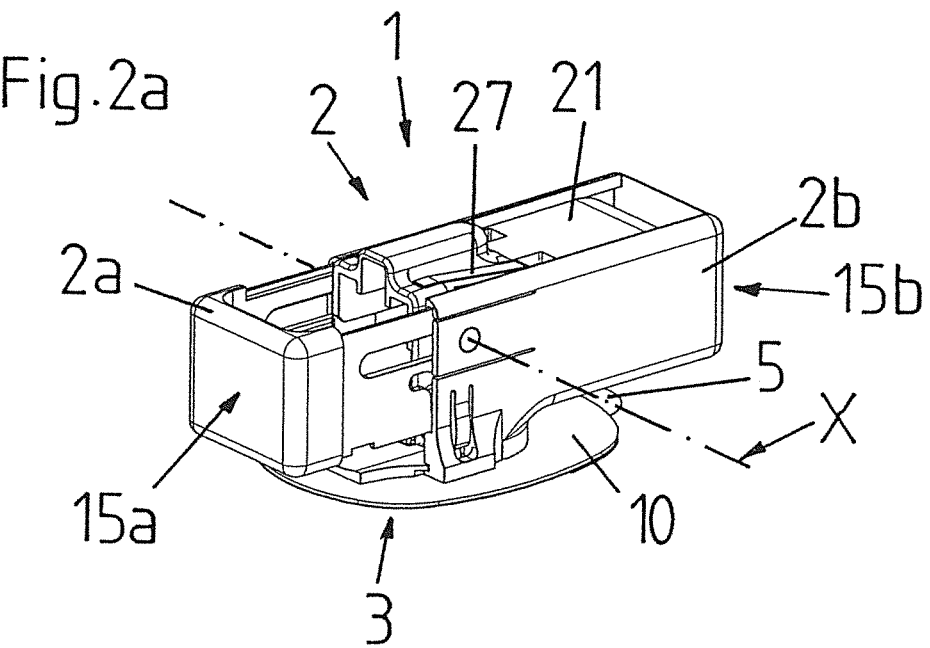
FIG. 2a illustrates a perspective view of the device of FIG. 1a in a second state according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

The present disclosure concerns a device for inserting one or more insertion members (of the same or of different kind) having a puncturing tip, such as, for example, infusion cannulas and/or sensor tips, into body tissue and, at the same time, affixing them to the skin. The device can comprise a housing, an insertion arrangement and a drive.

The housing can provide at least one contact face for placing the device onto the skin. This contact face can carry a layer of skin compatible glue for affixing to the skin. Such skin compatible glues are known to persons skilled in the art. The layer of skin compatible glue may be covered by a removable protecting layer, such as, for example, a protective film which before use can be removed in order to make the glue accessible.

The insertion arrangement can be movably arranged within the housing and can comprise one or more insertion members that can be inserted into the tissue. It can furthermore comprise a holder element which can be fixedly connected to each of the one or more insertion members that can remain for a long period inside the tissue. This connection can be established for example, by bonding or by a one piece design.

The drive can be arranged within the housing of the device. The drive can effect an insertion movement of the insertion arrangement from a first position, in which the puncturing tips of the one or more insertion members can be set back relative to the contact face of the housing, into a second position, in which the puncturing tips can protrude beyond the contact face. Thus, when the device during the insertion movement of the insertion arrangement is placed with its contact face onto the skin of the body of a patient, the puncturing tips of the one or more insertion members can penetrate the skin and the insertion members can be inserted into the tissue.

The contact face of the housing can be formed by a base plate which can be affixed to the housing in such a manner that after the insertion movement has been performed and the insertion arrangement is in the second position, it can be detached from the rest of the housing. For embodiments in which additional members are temporarily employed in the insertion process which are not intended to remain inside the tissue for a long period such as, for example, guiding members for stiffening soft members to be inserted into the tissue, the base plate can be detachable from the housing only after these additional members have been removed or retracted, especially in cases in which the additional member in the non-removed or non-retracted position can impede the detaching. The holder element of the insertion arrangement can comprise a coupling for coupling to a corresponding coupling on the base plate in order to establish a connection between the insertion arrangement and the base plate to safely hold the insertion arrangement to the base plate at the body of a patient.

The connection between the coupling of the holder element of the insertion arrangement and the corresponding coupling of the base plate can automatically be established when, by performing the insertion movement, the insertion arrangement is brought into the second position.

It can be possible to affix a base plate, which is used to safely hold the insertion member at the body of the patient, at the desired application site to the skin prior to the insertion of the insertion member into the tissue. This can have the advantage that the base plate does not need to be accelerated by the drive during the insertion movement. Thus, less driving energy may be needed for effecting the insertion movement so that the insertion movement can take place with a higher speed, resulting in a further reduction of the pain associated with the piercing of the skin compared to known insertion devices. Furthermore, this can offer the advantage that, before the insertion of the insertion member into the tissue, the base plate can properly be affixed to the skin at the application site by pressing the device with the layer of skin compatible glue against the skin by hand, thus, the risk of a flexing of the insertion member or of an irritation of the application site due to a movement of the inserted insertion member caused by an insufficient fixation of the base plate can practically be eliminated.

In one embodiment, the base plate can automatically be separated from the rest of the housing when the insertion arrangement is brought into the second position, thus, the rest of the housing can be removed from the base plate without further handling steps. Through such a design, the handling of the device can further be facilitated and the risk of an irritation of the application site can be further reduced.

In another embodiment, at least one of the one or more insertion members of the insertion arrangement can comprises, as the part that is intended to remain inside the tissue for a long period, a soft member and additionally a guiding member can be associated with this soft member for temporarily stiffening the soft member during its insertion into the tissue. The guiding member can form the puncturing tip for piercing the skin when inserting this insertion member into the tissue. The soft member can be fixedly connected with the holder element. After the insertion movement of the insertion arrangement has been performed, the soft member can be coupled to the base plate by the coupling of the holder element and the associated guiding member can be coupled to the rest of the housing in such a manner that, when the rest of the housing is removed from the base plate, the guiding member can be retained in the rest of the housing and can be removed with the rest of the housing. All insertion members of the insertion arrangements may comprise a soft member which can remain for a longer period inside the tissue and an associated guiding member for temporarily stiffening the soft member during insertion into the tissue. Such embodiments can have the advantage that an irritation of the application site during the application period may be kept at a minimum since the parts of the insertion members which stay in the tissue of the body are soft elements, that is can be elements that have a certain flexibility so that they can follow movements of the body tissue.

In embodiments in which at least one of the one or more insertion members comprises a soft member which is intended for remaining for a long period inside the tissue and an associated guiding member for temporarily stiffening the soft member during insertion into the tissue, the device may further comprises a drive for effecting, after the insertion movement of the insertion arrangement, a retracting movement of the guiding member from the second position into a third position. In this third position, the puncturing tip of the insertion member comprising the soft member and the associated guiding member can be set back relative to the contact face of the housing so that, when during the retracting movement the soft member is held in the second position by the holder element coupled to the base plate, the guiding member can be separated from the soft member. After the insertion movement of the insertion arrangement is performed, automatically the retracting movement of the at least one guiding member can be performed.

With such devices, the insertion of a soft member, such as, for example, a soft cannula, into the tissue can be easy and safe even for unskilled persons since the risk of an irritation of the puncture site due to an unskilled removal of the guiding member as well as the risk of an unintended contact with the contaminated guiding member or even of an injury caused by a contact with the puncturing tip can be virtually eliminated.

Furthermore, when the guiding member after the retracting movement is arranged in the rest of the housing in the third position and the rest of the housing has been removed from the soft member, the guiding member cannot be separated from the rest of the housing or can be separated from the rest of the housing without contacting it or a holder element fixedly connected to it. The first alternative can be somewhat favorable if the housing is a disposable part so that the contaminated guiding member can be disposed together with the rest of the housing. The second alternative can be somewhat favorable if the rest of the housing is intended to be used several times and the guiding member for disposal is separated from the housing. In both cases, the advantage can be that for disposal of the contaminated guiding member only the housing may need to be contacted by hand, thus, the risk of a contact with the contaminated guiding member and, in particular, with its puncturing tip can be further reduced.

It may be furthermore advantageous, in which at least one of the one or more insertion members of the insertion arrangement can comprise a soft member and an associated guiding member, that the soft member can be a soft cannula and the associated guiding member can be a guiding needle extending through the fluid channel of the soft cannula for temporarily stiffening it during introduction into the tissue. In the case in which the guiding needle can be retracted into a third position, when the retracting movement of the at least one guiding needle is performed while the soft cannula is held in the second position by the holder element coupled to the base plate, the guiding needle can be pulled out of the fluid channel of the at least one soft cannula.

In still a further embodiment, the device further can comprise a activator for activating the drive. The activator can be actuated by the user with one hand. This can considerably facilitate the operation of the device and can furthermore permit its use for the application of insertion members in body regions which can be difficult to access or which cannot be accessible with both hands.

In still a further embodiment, the drive may comprise at least one energy source for providing driving energy for the insertion movement and/or, where applicable, for the retracting movement, such as, for example a pre-tensioned spring element, a pressurized gas reservoir, a battery, an accumulator and/or a pyrotechnical propelling charge.

Additionally or alternatively, the drive may comprise at least one energy storing element for providing driving energy for the insertion movement and/or, where applicable, for the retracting movement, which, before use of the device, can be charged with energy. The at least one energy storing element may comprises a spring element that can be pre-tensioned and/or a gas reservoir that can be pressurized. Such devices can be comfortable to use and can allow an insertion movement with defined insertion speed and insertion force.

In case of embodiments in which the device comprises at least one energy storing element, the device may further comprise manual energy charging which can be actuated by hand to transfer power generated by the muscles of the hand of a user to the at least one energy storing element. The manual energy charging may be actuated with one hand. Such embodiments can have the advantage that they may be independent from foreign energy sources and, if so, can be operated everywhere and at any time.

The manual energy charging can comprise a slide-shaped, or button-shaped, element that can be slid along or pushed into the housing or can comprise two housing elements that can be pushed into or towards each other. The direction of sliding along the housing, pushing into the housing or pushing into or towards each other may be transverse, such as perpendicular, to the direction of the insertion movement of the insertion arrangement. This can considerably facilitate the integration of the manual energy charging into the device and the operation of the device by the user.

In embodiments in which the device comprises an activator that can be actuated by the user with one hand and furthermore can comprise at least one energy storing element and manual energy charging for charging the energy storing element, the activator and the manual energy charging may be designed in such a manner that charging of the at least one energy storing element and activating of the drive for effecting the insertion movement can be effected through the same manual operation.

In embodiments of the device designed to perform a retracting movement of one or more guiding members of the insertion arrangement, the drive for effecting the insertion movement can be the same or can be a different drive than the drive for effecting the retracting movement. Furthermore, the energy for the insertion movement and the energy for the retraction movement can commonly or can separately be provided by one or by several energy sources of the same kind or of different kind, such as, for example by a combination of hand energy and pressurized gas and/or pre-loaded springs. For example, a pre-loaded spring can provide the insertion energy while the hand can provide the retraction energy.

In still a further embodiment, the insertion arrangement in the first position can be oriented substantially perpendicular to a plane formed by the at least one contact face of the housing and the insertion movement can be a linear movement along an axis perpendicular to the plane. The insertion member can be inserted into the tissue perpendicular to the surface of the skin of the body which can be advantageous.

In the above case, it can be favorable that, in an initial position, the insertion arrangement can be oriented substantially parallel to the plane formed by the at least one contact face of the housing and, before the insertion movement can be performed, can be pivoted from the initial position into the first position. This can make it possible to provide devices which in the original non-used state have small packaging.

If additionally the device further comprises an activator for activating the drive, upon an actuating of the activator, the insertion arrangement can automatically be moved from the initial position into the first position facilitating the use of the device.

In a further embodiment, the device can be formed by an inserting device having the housing without base plate and the drive, by an insertion head, such as, for example, an infusion set that can provide the insertion arrangement and by a base plate which can be part of the insertion head or can be separate. The insertion head can be received within the inserting device for being applied by it to the body of the patient and the base plate can be affixed to the housing in order to be pressed with the housing against the skin. The inserting device can be designed in such a manner that, after the application of the insertion head, its separation from the base plate and, where applicable, the removal of additional members of the insertion head which have been retained in it, such as, for example, guiding members of the applied insertion head, it can receive another insertion head for applying it to the body. Thereby, the amount of waste generated in therapies employing the frequent insertion of insertion members into the body of a patient can be kept at a minimum.

The device can be used for applying an infusion set to the body of a patient, for example an infusion set having a soft cannula.

A method of inserting one or several insertion members having a puncturing tip, in particular having at least one infusion cannula and/or at least one sensor tip, into the tissue of the body of a patient and affixing it to the skin is also disclosed. The device can be placed with its layer of skin compatible glue onto the skin at the desired application site for affixing the base plate to the body. The drive can be activated, thereby effecting the insertion movement of the at least one insertion member into the body tissue and the coupling of the one or more insertion members to the base plate. The rest of the housing can be separated from the base plate while the parts of the insertion members which are intended to remain for a longer period within the tissue remain inserted in the tissue and can be affixed to the skin by the base plate.

The application of an infusion set to the body of a patient can be performed, even by unskilled persons, in an extremely safe and easy manner, without the risk of a flexing of the insertion member or of an irritation of the application site due to a movement of the inserted insertion member caused by an insufficient fixation of the base plate. Furthermore, the insertion movement can take place with a higher speed compared to known methods, resulting in a further reduction of the pain associated with the piercing of the skin.

In an embodiment of the method, the insertion member used in the method can be a soft cannula and the guiding member used can be a guiding needle which, at the time the soft cannula is inserted into the tissue, can extend through the fluid channel of the soft cannula.

The device can insert a soft member into the body tissue. The device can comprise a housing having at least one contact face for placing the device onto the skin. Furthermore, the device can comprise an insertion arrangement which can be movably arranged within the housing and can provide the soft member to be inserted into the tissue. The soft member can be an element which has certain flexibility so that, in the inserted state, it can follow certain movements of the body tissue. The insertion arrangement can furthermore provide a guiding member for temporarily stiffening the soft member during introduction into the tissue. This guiding member can also form a puncturing tip for puncturing the skin when inserting the soft member with its help into the tissue.

The device can further comprise a drive for effecting an insertion movement of the insertion arrangement from a first position, in which the puncturing tip of the guiding member is set back relative to the contact face, into a second position, in which the puncturing tip protrudes beyond the contact face of the housing, so that, when the insertion movement is performed while the device is placed with its contact face on the body of the patient, the soft member together with the guiding member can be inserted into the tissue.

Furthermore, the device can comprise a drive for effecting, after the insertion movement of the insertion arrangement has been performed, a retracting movement of the guiding member from the second position into a third position, in which its puncturing tip is set back relative to the contact face of the housing, so that, when the retracting movement is performed while the soft member is held in the second position, the guiding member can be separated from the soft member. The drive for effecting the insertion movement can be the same or can be a different drive than the drive for effecting the retracting movement.

Furthermore, after the insertion arrangement has reached the second position at the end of the insertion movement, the retraction movement of the guiding member can automatically be performed. Thus, upon an activation of the drive for the insertion movement, the insertion movement of the insertion arrangement can be performed and after that the drive for the retracting movement can automatically be activated and the retraction movement of the guiding member can be performed.

In one embodiment, the soft member can be a soft cannula and the guiding member can be a guiding needle extending through the fluid channel of the soft cannula for temporarily stiffening it during introduction into the tissue. A free end of the guiding needle can protrude out of the soft cannula thereby forming the puncturing tip for puncturing the skin of the body of the patient when inserting the soft cannula into the tissue. During the retracting movement of the guiding needle from the second position into the third position, the soft cannula can be held in the second position and the guiding needle can be pulled out of the fluid channel of the soft cannula by the drive. In such embodiments, which typically are employed to apply infusion sets for the infusion of a liquid medicine, such as, for example, insulin, to patients; the advantages of a device according to the present disclosure can become apparent.

In another embodiment, the insertion arrangement can comprise a base plate which can be coupled to the soft member. This base plate can carry, on its side which during the insertion movement is facing towards the puncturing tip of the guiding member, a layer of skin compatible glue for affixing the soft member to the skin of the body of the patient when inserting it into the tissue. The layer of skin compatible glue may be covered by a protection layer, such as, for example a protective film, which may be removed prior to performing the insertion movement of the insertion arrangement. Such embodiments can be especially suitable for being formed by using commercially available infusion sets in which a soft cannula can be through material bonding connected with a base plate carrying a layer of skin compatible glue.

In another embodiment, the contact face of the housing can carry a layer of skin compatible glue for affixing it to the skin. Also in this embodiment, the layer of skin compatible glue may be covered by a protection layer, such as, for example a protective film, which may be removed prior to the use of the device. The contact face can be formed by a base plate which in a releasable manner can be fixed to the rest of the housing. In this embodiment, the insertion arrangement can comprise a coupling connected with the soft member for coupling the soft member to the base plate when the insertion arrangement is moved into the second position. In this embodiment, the base plate, which can be used to affix the soft member to the body of the patient, can be affixed with its layer of skin compatible glue at the desired application site to the skin prior to the insertion movement of the insertion arrangement. This can offer the advantage that the base plate does not need to be accelerated by the drive during the insertion movement so that less driving energy may be needed for effecting the insertion movement or the insertion movement can take place with a higher speed, resulting in a reduction of the pain associated with the piercing of the skin.

In this case, the base plate can be automatically separated from the housing when the insertion arrangement is brought into the second position or latest when the guiding member is brought into the third position, so that the housing together with the guiding member received in it can without further handling steps be removed from the base plate and the soft member coupled to it. Through such a design, handling of the device can be as easy and safe as possible.

In another embodiment, when the guiding member after the retracting movement is held in the housing in the third position and the housing has been removed from the soft member, the guiding member can be contained within the housing in such a manner that its puncturing tip does not protrude out of the housing. Through this, the risk of contacting the contaminated guiding member and in particular the risk of an injury caused by the contaminated puncturing tip thereof can be considerably reduced.

In one embodiment, when the guiding member after the retracting movement is held in the housing in the third position and the housing has been removed from the soft member, the guiding member cannot be separated from the housing or can be separated from the housing without contacting the guiding member or a holder element fixedly connected with the guiding member. The first alternative can be somewhat favorable if the housing is designed as a disposable part so that the contaminated guiding member can be disposed off together with the housing. The second alternative can be somewhat favorable if the housing is intended to be used several times and the guiding member for disposal is separated from the housing. In both cases the advantage can be arrived at that for disposal of the contaminated guiding member only the housing needs to be contacted by hand, thus, the risk of a contact with the contaminated guiding member during or of an injury caused bit its puncturing tip can be further reduced.

In another embodiment, the device may be formed by an inserting device which can provide the housing and the drive and by an insertion head, such as, for example an infusion set, which can provide the insertion arrangement. The insertion head can be received within the inserting device for being applied by it to the body. The inserting device can be designed in such a manner that, after the application of the insertion head and the removal of the guiding member from its housing, it can receive another insertion head for applying it to the body of a patient. Thereby, the amount of waste generated in therapies employing the frequent insertion of soft members into the body of a patient can be kept at a minimum. A device can typically be used for applying an infusion set with a soft cannula to the body of a patient.

In one embodiment, the device can be placed with at least one contact face onto the skin at the desired application site. The drive of the device can be activated, thereby effecting the insertion movement of the insertion arrangement into the tissue and after that the retracting movement of the guiding member. The housing with the guiding member contained in it can be separated from the soft member while the soft member remains inserted in the tissue of the body of the patient. A soft member can be inserted into the body even by unskilled or hampered persons in an easy and safe manner, without the risk of an irritation of the application site through an unskilled removal of the guiding member from the inserted soft member and without the risk of an unintended contact with the contaminated guiding member or of an injury. In an embodiment of the method, the soft member can be a soft cannula and the guiding member used can be a guiding needle, which, at the time the soft cannula can be inserted into the tissue, can extend through the fluid channel of the soft cannula.

Referring initially to FIGS. 1*a* and *b*, a device 1 is shown in a first state (original state), once in a perspective side view (FIG. 1*a*) and once in a perspective longitudinal section (FIG. 1*b*). As can be seen, the device 1 can comprise a housing 2 substantially formed by two housing elements 2*a*, 2*a* which can be pushed into each other for operating the device and a drive unit housing 21 can be arranged within the second housing element 2*b*, as shown in the figures. On the bottom side, the second housing element 2*b* can carry a base plate 10 providing a contact face 3 for placing the device 1 onto the skin. This contact face 3 can carry a layer 4 of skin compatible glue for affixing the base plate 10 to the skin, which the layer 4 can be covered by a removable protecting film 5 to be removed before the first use of the device 1.

Within the housing 2, 2*a*, 2*b*, a cannula arrangement 6 can be arranged in a movable manner and can comprise a soft cannula 11 for being inserted into the tissue and a guiding needle 12 extending through the fluid channel of the soft cannula 11 for temporarily stiffening it during introduction into the tissue. The soft cannula 11 together with the guiding needle 12 can form an insertion member 11, 12. The soft cannula can be the part of this insertion member that is intended to remain inside the tissue for a long period. The guiding needle 12 at the free end of the cannula arrangement 6 can protrude out of the soft cannula 11, thereby forming a puncturing tip 9 for puncturing the skin when inserting the soft cannula 11 with the help of the guiding needle 12 into the tissue. The soft cannula 11 at its end facing away from the puncturing tip 9 can be fixedly connected through material bonding to an adapter housing 7, or holder element 7, providing a port 16 for connecting a catheter to the housing 7 and a fluid channel 17 extending inside the housing 7 between the soft cannula 11 and the port 16, for fluidically connecting the catheter with the soft cannula 11. The guiding needle 12 at its end facing away from its puncturing tip 9 can protrude through a septum 19 provided by the adapter housing 7 into a holder element 14 to which it can be fixedly connected. The holder element 14 can, in a slidable manner, receive in a guiding sleeve 18 which in turn in a slidable manner can be guided inside the drive unit housing 21 which in a tiltable manner around an axis X can be arranged inside the second housing element 2*b*. The soft cannula 11 and the adapter housing 7 can be carried by the guiding needle 12. In this state, the cannula arrangement 6 can be oriented substantially parallel to a plane formed by the contact face 3. The device 1 can comprise helical springs 8, 13 arranged in a coaxial manner within the drive unit housing 21.

Figure 2B:
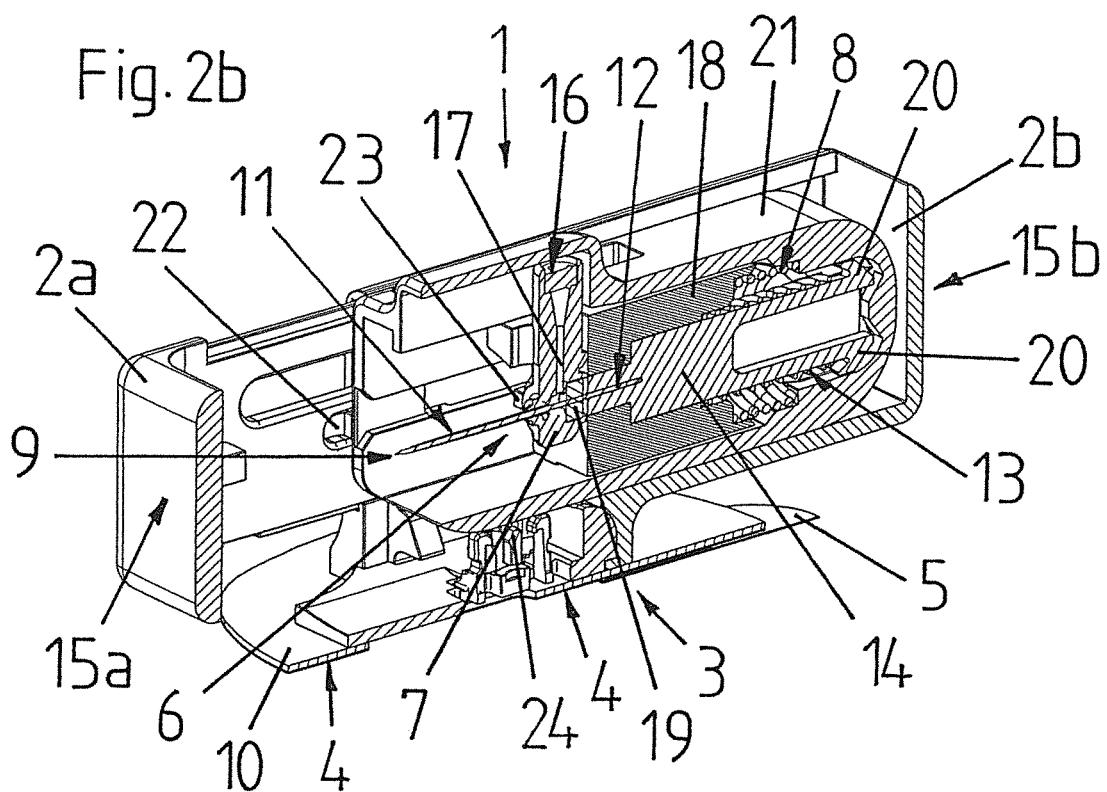
FIG. 2b illustrates a perspective longitudinal section of the device of FIG. 2a according to an embodiment of the present disclosure.

For operating the device 1, the front faces, or activators, 15*a*, 15*b* of the two housing elements 2*a*, 2*b* can be contacted with the fingertips of the trigger finger and thumb of one hand of the operator and can be pressed towards each other. By doing so, the two housing elements 2*a*, 2*b* can be pushed into each other and the guiding sleeve 18, which carries the cannula arrangement 6, can be pushed by the first housing element 2*a* into the drive unit housing 21 against the force of the two springs 8, 13, both can have one of their two ends abut against the guiding sleeve 18 and their other ends abut against an end of the drive unit housing 21. During this movement of the guiding sleeve 18, the holder element 14 can travel through the centers of the springs 8, 13 and at the end, when both springs 8, 13 are completely pre-tensioned, can snap with resilient hook elements 20 formed at its end behind the end of the inner spring 13 which can abut against the end of the drive unit housing 21. At the same time, latching rockers 27 arranged at the drive unit housing 21 can snap behind lugs 28 arranged at the guiding sleeve 18, thereby arresting the guiding sleeve 18 in a state in which the springs 8, 13 can be pre-tensioned. This situation, in which the first housing element 2*a* has been pushed by about two thirds of its possible travel into the second housing element 2*b*, is shown in the FIGS. 2*a* and 2*b*, in a perspective side view (FIG. 2*a*) and in a perspective longitudinal section (FIG. 2*b*).

Figure 3A:
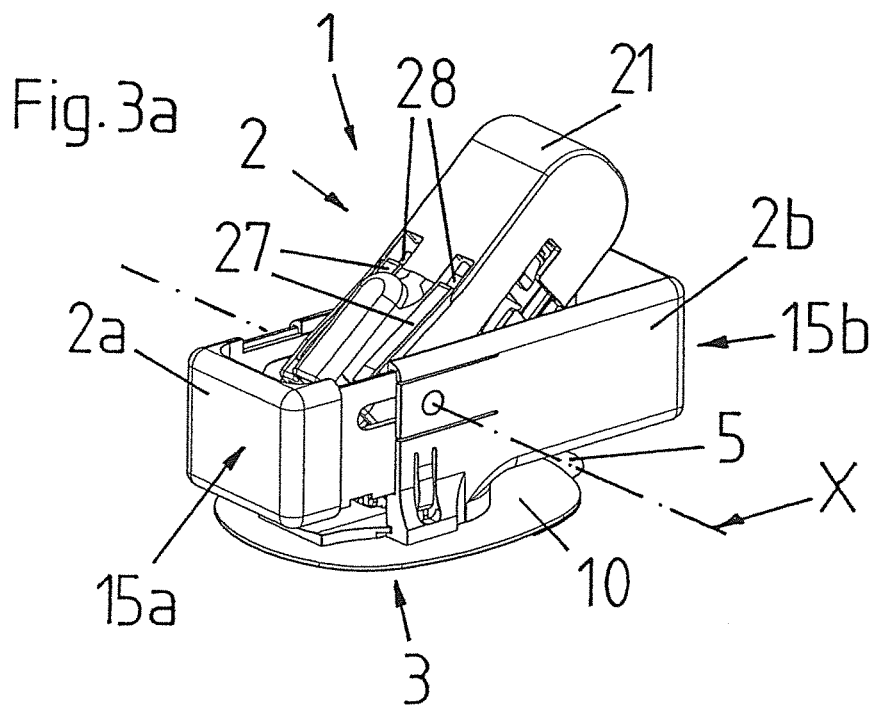
FIG. 3a illustrates a perspective view of the device of FIG. 1a in a third state according to an embodiment of the present disclosure.
Figure 3B:
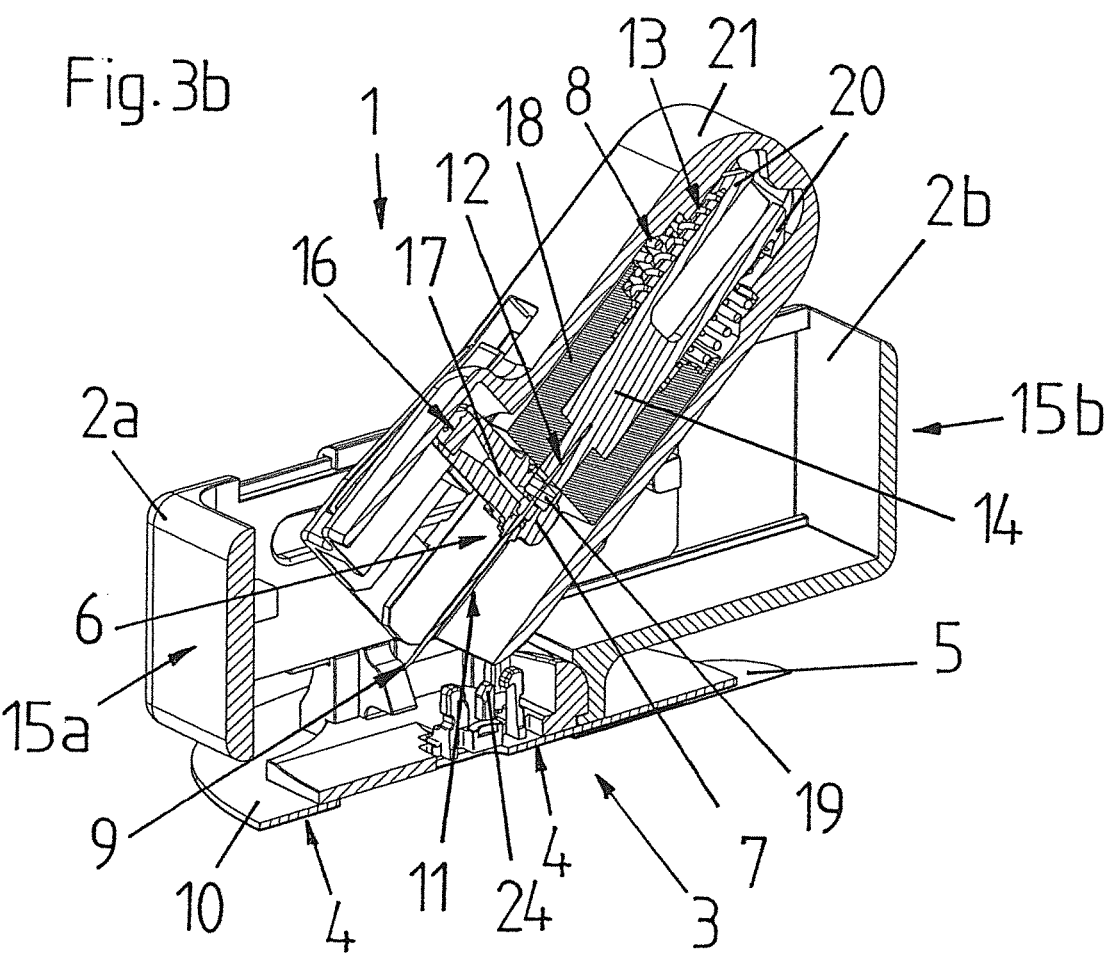
FIG. 3b illustrates a perspective longitudinal section of the device of FIG. 3a according to an embodiment of the present disclosure.

By further pushing the two housing elements 2*a*, 2*b* inside each other, the drive unit housing 21 with the cannula arrangement 6 carried by it is can be tilted around its tilting axis X from its initial position, in which the cannula arrangement 6 can be oriented substantially parallel to a plane formed by the contact face 3, over an intermediate position shown in the FIGS. 3*a* and 3*b* into its operating position, or first position, shown in the FIGS. 4a and 4b, in which the cannula arrangement 6 can be oriented substantially perpendicular to the plane formed by the contact face 3. In this situation, the puncturing tip 9 of the guiding needle 12 can be set back relative to the contact face 3. The tilting movement of the drive unit housing 21 can be effected by a pivot formed at the drive unit housing 21 which can travel in a guiding slot 22 in the first housing element 2a. As is visible especially in FIG. 4a, in this state the housing elements 2a, 2b can almost be fully pushed towards each other.

By completely pushing the two housing elements 2a, 2b towards each other, the latching rockers 27 can be actuated, thereby releasing the lugs 28. The force of the pre-tensioned outer spring 8 can now drive the guiding sleeve 18 and with it the cannula arrangement 6 in a direction substantially perpendicular to the plane formed by the contact face 3 towards the base plate 10, where at the end of this insertion movement, the adapter housing 7 with protrusions 23 formed at its outside can snap behind resilient hook elements 24 formed at the base plate 10 and thereby in a positive manner can be coupled to the base plate 10. In this second position, which is shown in the FIGS. 5a, 5b and 5c, the puncturing tip 9 and large portions of the guiding needle 12 as well as of the soft cannula 11 can protrude beyond the contact face 3 of the base plate 10.

Figure 5A:
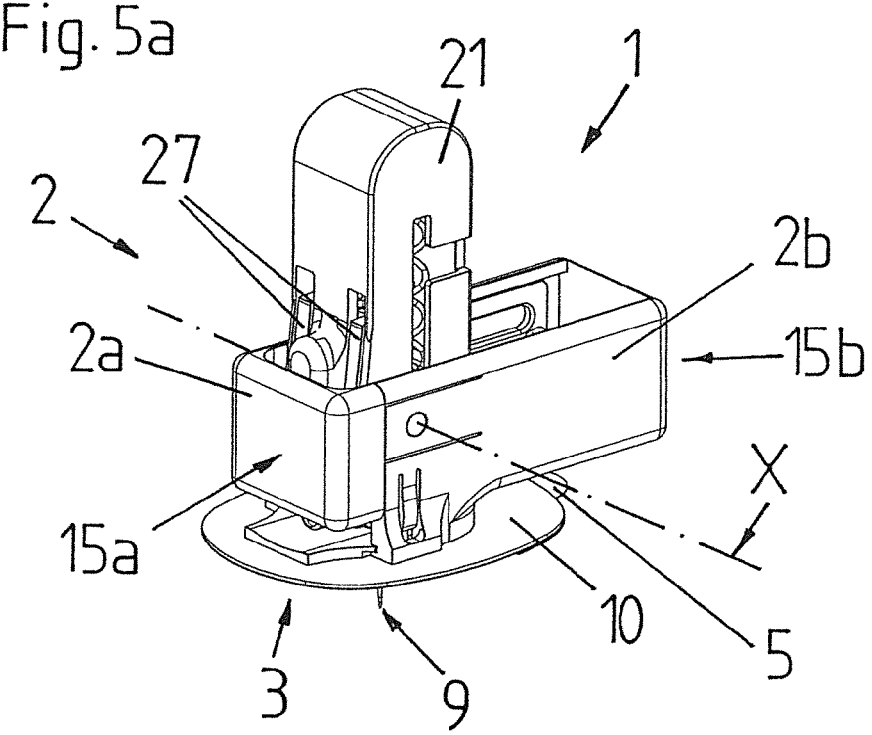
FIG. 5a illustrates a perspective view of the device of FIG. 1a in a fifth state according to an embodiment of the present disclosure.
Figure 5B:
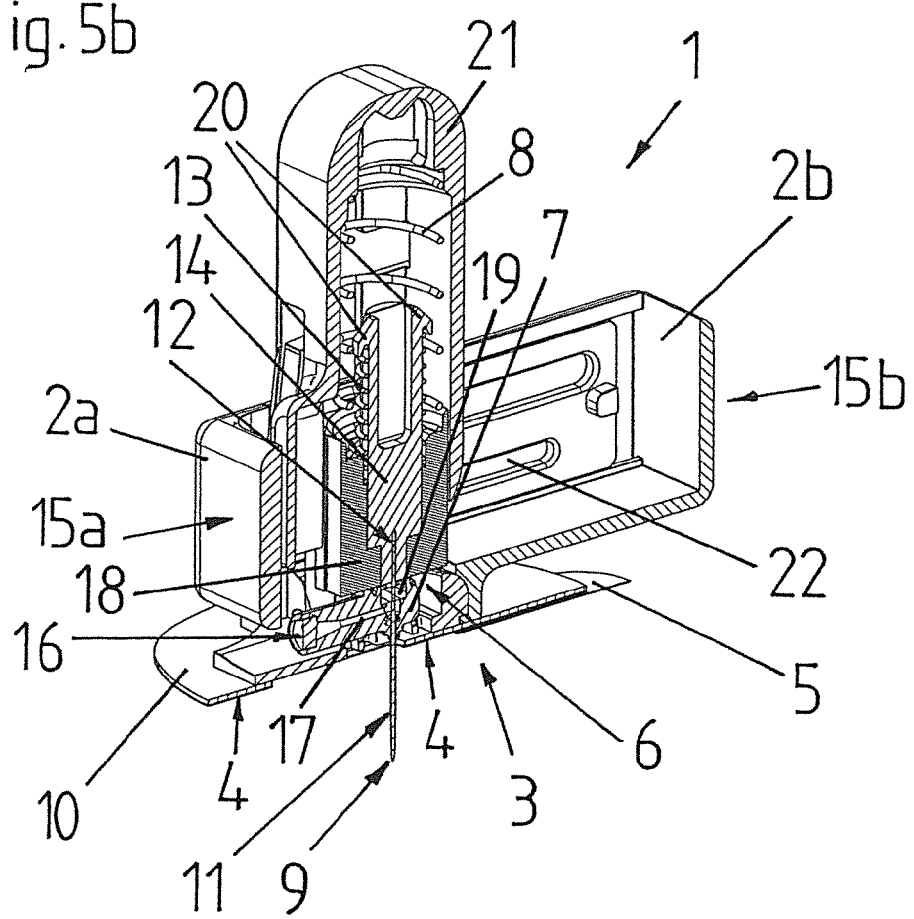
FIG. 5b illustrates a perspective longitudinal section of the device of FIG. 5a according to an embodiment of the present disclosure.
Figure 6:
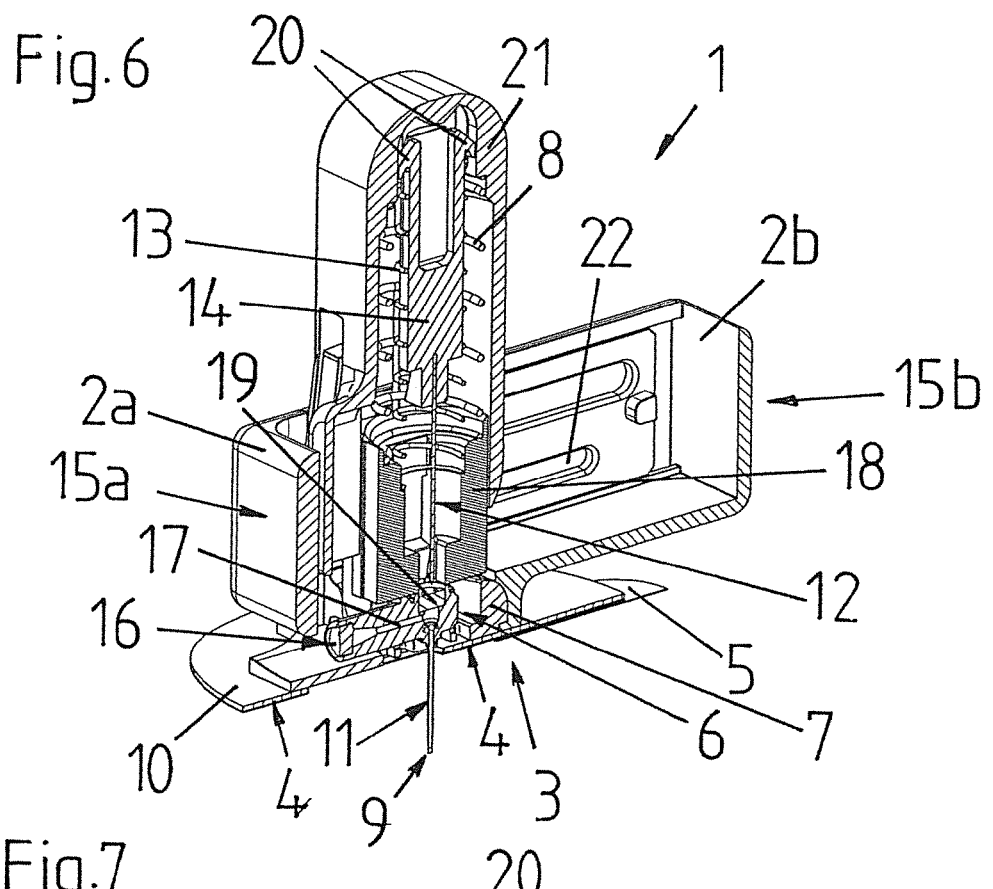
FIG. 6 illustrates a perspective longitudinal section of the device of FIG. 1a in a sixth state according to an embodiment of the present disclosure.
Figure 7:
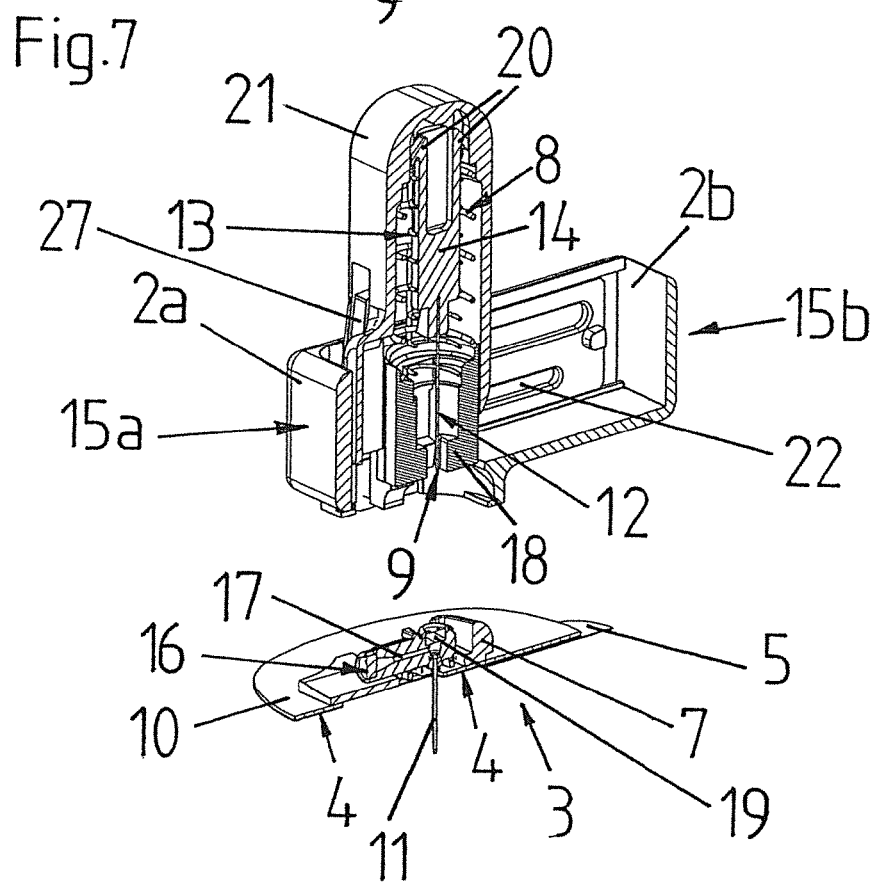
FIG. 7 illustrates a perspective longitudinal section of the device of FIG. 1a in a seventh state according to an embodiment of the present disclosure.

As can be seen in FIG. 5c, which shows a cross section of the device 1, the guiding sleeve 18 can comprise two resilient hook elements 25, which can abut with contact surfaces 26 that can be inclined relative to the direction of the insertion movement against corresponding contact surfaces formed at the holder element 14 of the guiding needle 12. During the insertion movement, the hook elements 25 can be radially blocked by guiding surfaces of the drive unit housing 21, so that during the insertion movement, the holder element 14 in a positive manner in movement direction can be coupled to the guiding sleeve 18. In the end position of the insertion movement shown in the FIGS. 5a to 5c, the hook elements 25 can be free to radially expand. In this situation, the holder element 14 can be pulled upwards through the force of the inner spring 13, thereby radially expanding the hook elements 25 by its inclined contact surfaces (see the arrows in FIG. 5c) and pulling the guiding needle 12 out of the soft cannula 11 and out of the septum 19 of the adapter housing 7, i.e., the retracting movement, into a third position in which its puncturing tip 9 can be set back relative to the contact face 3. In this situation, which is shown in FIG. 6, the second housing element 2b can be detached from the base plate 10 and can, together with the guiding needle 12 contained therein, be removed from the base plated 10 without any risk that its puncturing tip can be contacted by hand and can cause an injury to persons. This situation is shown in FIG. 7.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

For the purposes of describing and defining the present disclosure, it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. A device for inserting at least one insertion member having a puncturing tip into tissue of a patient and for affixing the at least one insertion member to the patient's skin, the device comprising:

a housing having at least one contact face for affixing the device onto the patient's skin;

an insertion arrangement movably arranged within the housing comprising the at least one insertion member to be inserted into the tissue and a holder element fixedly connected with at least a part of the at least one insertion member which is intended to remain for a long period inside the tissue; and a drive arranged within the housing for effecting an insertion movement of the insertion arrangement from a first position, in which the puncturing tip of the at least one insertion member is pulled back relative to the contact face, into a second position, in which the puncturing tip of the at least one insertion member protrudes beyond the contact face, so that the at least one insertion member is inserted into the tissue when the device is placed with its contact face on the patient during the insertion movement of the insertion arrangement, the insertion movement being a linear movement along an axis perpendicular to a plane formed by the at least one contact face, wherein the contact face is formed by a base plate affixed so that, after the insertion movement has been performed, the base plate detaches from the housing and wherein the holder element of the insertion arrangement is coupled to the base plate when the insertion arrangement by the insertion movement is brought into the second position, wherein in an initial position, the insertion arrangement is oriented substantially parallel to said plane formed by the at least one contact face and before the insertion movement can be performed is pivoted from the initial position into a first position, in which the insertion arrangement is oriented substantially perpendicular to said plane formed by the at least one contact face, by tilting a drive unit housing, the tilting being effected by a pivot formed at a drive unit housing travelling in a guide slot of a first housing element;

wherein the at least one insertion member of the insertion arrangement comprises at least one soft member for insertion into the tissue and at least one guiding member for temporarily stiffening the at least one soft member during insertion into the tissue, wherein the guiding member forms the puncturing tip for puncturing the skin when inserting the at least one insertion member into the tissue, wherein the holder element is fixedly connected with the at least one soft member and wherein, after the insertion movement of the insertion arrangement the at least one soft member is coupled to the base plate by the holder element, the at least one guiding member is coupled to the housing so that, when the housing is removed from the base plate, the at least one guiding member is retained in the housing and is removed with the housing; and wherein the drive further effects, after the insertion movement of the insertion arrangement, a retracting movement of the at least one guiding member from the second position into a third position, in which the puncturing tip of the at least one guiding member is pulled back relative to the contact face, so that, when the at least one soft member is held in the second position by the holder element coupled to the base plate, the at least one guiding member is separated from the at least one soft member.

2. The device according to claim 1, wherein the at least one insertion member having a puncturing tip is an infusion cannula and/or sensor tip.

3. The device according to claim 1, wherein the contact face has a skin compatible glue layer for affixing to the skin.

4. The device according to claim 3, wherein the skin compatible glue layer is covered by a removable protecting layer.

5. The device according to claim 1, wherein the base plate automatically separates from the housing when the insertion arrangement is brought into the second position.

6. The device according to claim 1, wherein the device, after the insertion movement of the insertion arrangement is performed, automatically performs the retracting movement of the at least one guiding member.

7. The device according to claim 1, wherein when the at least one guiding member after the retracting movement is arranged in the housing in the third position and the housing has been removed from the at least one soft member, the at least one guiding member cannot be separated from the housing or can be separated from the housing without contacting it or the holder element fixedly connected with the at least one guiding member.

8. The device according to claim 1, wherein the at least one soft member comprises at least one soft cannula with a fluid channel and the at least one guiding member comprises at least one guiding needle extending through the fluid channel of the soft cannula for temporarily stiffening the soft cannula during introduction into the tissue.

9. The device according to claim 1, wherein the device further comprises an activator for activating the drive, wherein the activator is actuated by a user with one hand.

10. The device according to claim 9, wherein upon an activating of the activator, the insertion arrangement is automatically moved from the initial position into the first position.

11. The device according to claim 1, wherein the device is formed by an inserting device providing the housing and the drive, by an insertion head providing the insertion arrangement and by a base plate provided by the insertion head or provided separately, wherein the insertion head is received within the inserting device for being applied to the body by the inserting device and the base plate is fixed to the housing in order to be pressed with the housing against the skin, and wherein, after the application of the insertion head and its removal from the base plate, the inserting device can receive another insertion head for applying to the body.

12. A device for inserting a soft member into a body tissue of a patient, the device comprising:

a housing having at least one contact face for placing the device onto the skin of the patient;

an insertion arrangement movably arranged within the housing comprising the soft member to be inserted into the tissue and a guiding member for temporarily stiffening the soft member during introduction into the tissue, wherein the guiding member forms a puncturing tip for puncturing the skin when inserting the stiffened soft member with the guiding member into the tissue; and a drive for effecting an insertion movement of the insertion arrangement from a first position into a second position, wherein in the first position, the insertion arrangement is oriented substantially perpendicular to a plane formed by the at least one contact face and insertion movement is a linear movement along an axis perpendicular to the plane, and the puncturing tip is pulled back relative to the contact face in the first position and protrudes beyond the contact face in the second position, so that, when during the insertion movement the device is placed with its contact face on the body of a patient, the soft member together with the guiding member is inserted into the tissue of the body of the patient and for effecting, after the insertion movement of the insertion arrangement, a retracting movement of the guiding member from the second position into a third position, in which its puncturing tip is pulled back relative to the contact face, so that, when the soft member is held in the second position, the guiding member is separated from the soft member, wherein, after the insertion movement of the insertion arrangement has been performed, the retraction movement of the guiding member is automatically performed, and wherein in an initial position, the insertion arrangement is oriented substantially parallel to said plane formed by the at least one contact face and, before the insertion movement can be performed, must be pivoted from the initial position into the first position, by tilting a drive unit housing, the tilting being effected by a pivot formed at a drive unit housing traveling in a guiding slot of a first housing element.

13. The device according to claim 12, wherein the soft member is a soft cannula and the guiding member is a guiding needle extending through a fluid channel of the soft cannula for temporarily stiffening the soft cannula during introduction into the tissue, wherein the guiding needle at one end protrudes out of the soft cannula thereby forming the puncturing tip for puncturing the skin of the body of the patient when inserting the soft cannula into the tissue, and wherein the drive is designed in such a manner that when during the retracting movement of the guiding needle from the second position into a third position the soft cannula is held in the second position, the guiding needle is pulled out of the fluid channel of the soft cannula.

14. The device according to claim 12, further comprising, an activator for activating the drive and wherein the activator is configured to be actuated by the user with one hand.

15. The device according to claim 12, wherein the drive comprises separate first and second drives, the first drive effecting the insertion movement and the second drive effecting the retracting movement.

16. The device according to claim 12 further comprising an activator for activating the drive, wherein upon an actuating of the activator, the insertion arrangement is automatically moved from the initial position into the first position.

17. The device according to claim 16, wherein the insertion arrangement further comprises a base plate coupled to the soft member, which carries a layer of skin compatible glue for affixing the soft member to the skin when inserting it into the tissue.

18. The device according to claim 16, wherein the contact face of the housing carries a layer of skin compatible glue for fixing it to the skin and is formed by a base plate which in a releasable manner is fixed to the housing and wherein the insertion arrangement comprises coupling means connected with the soft member by which the soft member is coupled to the base plate when the insertion arrangement is moved into the second position.

19. The device according to claim 18, wherein the base plate is automatically separated from the housing when the insertion arrangement is brought into the second position or when the guiding member is brought into the third position so that rest of the housing together with the guiding member can be removed from the base plate.

20. The device according to claim 10, wherein when the guiding member after the retracting movement is held in the housing in the third position and the housing has been removed from the soft member, the guiding member is contained within the housing in such a manner that its puncturing tip does not protrude out of the housing.

21. The device according claim 12, wherein when the guiding member after the retracting movement is held in the housing in the third position and the housing has been removed from the soft member, the guiding member cannot be separated from the housing or can be separated from the housing without contacting the guiding member or a holder element fixedly connected with the guiding member.

22. The device according to claim 21, wherein the device is formed by an inserting device providing the housing and the drive and an insertion head, in particular an infusion set, providing the insertion arrangement, which insertion head is received within the inserting device for being applied to the body of the patient by the inserting device, and wherein after the application of the insertion head and the removal of the guiding member from the housing of the inserting device, the inserting device can receive another insertion head for applying the another insertion head to the body of a patient.

23. A method of inserting a soft member into the tissue of the body of a patient by using the device according to claim 12, comprising:
    placing the device with the at least one contact face onto the skin of the body at the desired application site;
    activating the drive, thereby effecting subsequently the insertion movement of the insertion arrangement and the retracting movement of the guiding member; and
    separating the housing with the guiding member from the soft member which remains inserted in the tissue of the body of the patient.

24. The method according to claim 23, wherein the soft member is a soft cannula and the guiding member is a guiding needle which during the insertion movement is extending through the fluid channel of the soft cannula.

* * * * *